United States Patent [19]

Pieper

[11] Patent Number: 4,735,748

[45] Date of Patent: Apr. 5, 1988

[54] PROCESS FOR MAKING PHOSPHONIC ACID DICHLORIDES

[75] Inventor: Werner Pieper, Kerpen, Fed. Rep. of Germany

[73] Assignee: Hoechst Aktiengesellschaft, Knapsack, Fed. Rep. of Germany

[21] Appl. No.: 930,661

[22] Filed: Nov. 13, 1986

[30] Foreign Application Priority Data

Nov. 26, 1985 [DE] Fed. Rep. of Germany ....... 3541627

[51] Int. Cl.$^4$ .............................................. C07F 9/42
[52] U.S. Cl. ................................................... 260/543 P
[58] Field of Search ..................................... 260/543 P

[56] References Cited

U.S. PATENT DOCUMENTS 2,847,469 8/1958 Dawson et al. ................. 260/543 P
4,155,932 5/1979 Masaki et al. .................... 260/543 P
4,213,922 7/1980 Maier .............................. 260/543 P

OTHER PUBLICATIONS

Patai, Saul *The Chemistry of Acyl Halides* (1972), Interscience, Publ. pp 43–44.

Lee, John B., *J. Am. Chem. Society* (1966) pp. 3340–3341.

*Primary Examiner*—Donald B. Moyer
*Assistant Examiner*—L. Hendriksen

[57] ABSTRACT

Phosphonic acid dichlorides of the general formula I

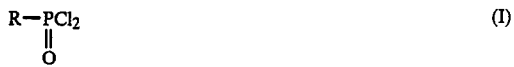

are made by reacting thionyl chloride with a phosphonic acid dialkylester of the general formula II

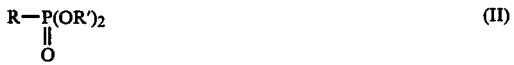

and using, as the catalyst, a compound of the general formulae III, IV or V

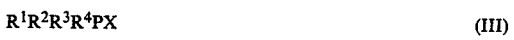

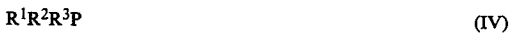

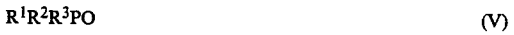

in which $R^1$, $R^2$ and $R^3$ each stand for identical or different alkyl groups or aryl groups having from 1 to 8 carbon atoms, X stands for chlorine or bromine, $R^4$ has the same meaning as $R^1$ through $R^3$ or stands for chlorine or bromine.

6 Claims, No Drawings

PROCESS FOR MAKING PHOSPHONIC ACID DICHLORIDES

The present invention relates to a process for making phosphonic acid dichlorides of the general formula I $$R\text{—}\underset{\underset{O}{\|}}{P}Cl_2 \quad (I)$$

in which R stands for a straight or branched, optionally halogen-substituted alkyl group, alkenyl group, aralkyl group or aryl group having from 1 to 12 carbon atoms, by reacting thionyl chloride with a phosphonic acid dialkylester of the general formula II $$R\text{—}\underset{\underset{O}{\|}}{P}(OR')_2 \quad (II)$$

in which R has the meaning given above and R' stands for a straight or branched, optionally halogen-substituted alkyl group having from 1 to 4 carbon atoms, in the presence of a catalyst.

It has been described that phosphonic acid dichlorides of the general formula I can be made by reacting a suitable ester of the general formula II with thionyl chloride (cf. Houben-Weyl "Methoden der organischen Chemie" E2, page 311 (1982) Verlag G. Thieme, Stuttgart). By the addition of an amine or amide such as triethylamine, pyridine or dimethylformamide, it is possible to accelerate the reaction and to increase, e.g. the methanephosphonic acid dichloride yield after distillation, to 94 %, compared with an 80 % yield obtained without catalyst addition (cf. U.S. Pat. No. 4,213,922).

This known process has a disadvantage associated with it which resides in the relatively long periods needed for effecting the reaction despite the addition of a catalyst. For making 1 mol methanephosphonic acid dichloride from methanephosphonic acid dimethylester and thionyl chloride in contact with dimethylformamide as a catalyst, it is invariably necessary for the reactants to be added over a dosing period of 2 hours and for them to be reacted over a period of a further 7.5 hours at boiling temperature in order to achieve a quantitative conversion.

A further disadvantage of this process resides in the use of catalysts which are liable due to their relatively high vapor pressure, to contaminate distilled matter obtained on purifying the phosphonic acid dihalides by distillation.

It is therefore highly desirable to provide catalytically active substances for the manufacture of phosphonic acid dichlorides by reacting a phosphonic acid diester with thionyl chloride, which permit the reaction to be carried out within distinctly shorter periods of time with high yields of desirably material and are practically not volatile so that the catalyst is not liable to contaminate the distilled product but is retained in the distillation residue and can be used jointly with the latter in further reaction batches.

To this end, the present invention unexpectedly provides for a compound of the general formulae III, IV or V $$R^1R^2R^3R^4PX \quad (III)$$

$$R^1R^2R^3P \quad (IV)$$

$$R^1R^2R^3PO \quad (V)$$

in which R1, R2 and R3 each stand for identical or different alkyl groups or aryl groups having from 1 to 8 carbon atoms, X stands for chlorine or bromine, R4 has the same meaning as R1 through R3 or stands for chlorine or bromine to be used as the catalyst in the process described hereinabove.

Tetrabutylphosphonium chloride or bromide as a compound of general formula III, triphenylphosphine as a compound of general formula IV, and trioctylphosphine oxide as a compound of general formula V should preferably be used as the catalyst.

It has also turned out advantageous to the use the phosphonic acid dialkylester, thionyl chloride and catalyst in a quantitative ratio of 1:2–3:0.001–0.1, preferably 1:2.5:0.01, and to effect the reaction at a temperature of from 70 to 150° C. at atmospheric pressure.

It is good practice first to prepare a mixture of phosphonic acid dialkylester and catalyst, heat the mixture to about 80° C. and add thionyl chloride thereto, or inversely first to prepare a mixture of thionyl chloride and catalyst, heat it to boiling and add the phosphoric acid ester thereto.

Gaseous reaction products formed during the reaction should suitable be incinerated or scrubbed with sodium hydroxide solution. At the end of the period needed for feeding the starting material, a post-reaction phase commences taking palce under reflux conditions at temperatures of at most 150° C. Next, thionyl chloride in excess and still dissolved gaseous reaction products, if any, are removed under vacuum. The remaining phosphonic acid dichloride can be purified by distilling it, if desired; the distillation residue contains practically quantitatively all of the catalyst used and should conveniently be used for further batches.

The compounds used in accordance with this invention are highly effective catalyst and compare favorably with the standard substances used heretofore as is evidenced by the distinctly shorter reaction periods and the fact that the phosphonic acid diester undergoes quantiative conversion to phosphonic acid dichloride.

The phosphonic acid dichlorides which are thus accessible under commercially attractive conditions are interesting reactive intermediates for use in synthesizing a wide variety of plant protecting and flame-retardant agents.

The following Examples illustrate the invention which is naturally not limited thereto;

EXAMPLE 1

A mixture of 297.5 g (2.5 mols) thionyl chloride and 2.95 g (0.01 mol) tetrabutylphosphonium chloride was placed and heated to boiling in a 500 ml multi-necked flask provided with a stirrer, dropping funnel, reflux condenser and internal thermometer. Next, 124 g (1 mol) methanephosphonic acid dimethylester was added dropwise within 2 hours. Towards the end of the dosing period, the temperature of the reaction mixture was found to have increased to 94° C. with continuous supply of heat. Methanephosphonic acid dichloride (23 P-%), methanephosphonic acid methylester chloride (54 P-%), polymethanephosphonic acid ester and chlorides (22 P-%) and tetrabutylphosphonium chloride (1 P-%) were found (31-P-NMR-spectroscopy) to have been formed at that moment.

This was followed by a 2 hour post-reaction period during which the temperature of the reaction mixture was gradually increased to 140° C. At that moment, the crude product consisted of 99 P-% methanephosphonic acid dichloride and 1 P-% tetrabutylphosphonium chloride, as determined by 31-P-NMR-spectroscopy.

The crude product was distilled and pure methanephosphonic acid dichloride was separated; the distillation residue contained methanephosphonic acid dichloride and all of the tetrabutylphosphonium chloride used as the catalyst.

EXAMPLE 2

297.5 g (2.5 mols) thionyl chloride was reacted as described in Example 1 with 124 g (1 mol) methanephosphonic acid dimethylester in the presence of 3.4 g (0.01 mol) tetrabutylphosphonium bromine. After a 2 hour dosing period and a 2 hour post reaction at up to 140° C., the reaction product was found to consist of 99 P-% methanephosphonic acid dichloride and 1 P-% tetrabutylphosphonium bromide from which it was separated by distillation.

EXAMPLE 3

119 g (1 mol) thionyl chloride was reacted as described in Example 1 with 125 g (0.5 mol) octanephosphonic acid diethylester in the presence of 1.5 g (0.005 mol) tetrabutylphosphonium chloride. After a 3 hour post reaction phase, the crude product was found (31-P-NMR-spectroscopy) to consist of 99 P-% octanephosphonic acid dichloride and 1 P-% tetrabutylphosphonium chloride from which it was separated by distillation.

EXAMPLE 4

119 g (1 mol) thionyl chloride was reacted as described in Example 1 with 125 g (0.5 mol) 2-chloroethanephosphonic acid bis-(2-chloroethylester) while adding 1.5 g (0.005 mol) tetrabutylphosphonium chloride. 31-P-NMR-spectroscopy indicated that the crude product consisted of 82 P-% 2-chloroethanephosphonic acid dichloride which was separated from the catalyst by distillation.

EXAMPLE 5

As described in Example 1, 297.5 g (2.5 mols) thionyl chloride and 8.9 g (0.01 mol) trioctylphosphine oxide were placed in the flask, heated to boiling and admixed within 1 hour with 124 g (1 mol) methanephosphonic acid dimethylester. After a further 1 hour with continuous supply of heat, the reaction temperature was at 137° C. 31-P-NMR-spectroscopy indicated that the crude product consisted of 99 P-% methanephosphonic acid dichloride and 1 P-% dichlorotrioctylphosphine from which it was separated quantitatively by distillation.

EXAMPLE 6

As described in Example 1, 297.5 g (2.5 mols) thionyl chloride and 2.6 g (0.01 mol) triphenylphosphine were placed in the flask, heated to boiling and admixed dropwise with 124 g (1 mol) methanephosphonic acid dimethylester. 2 hours after the end of the dosing period, the temperature was found to have increased to 140° C. with continuous supply of heat, 31-P-NMR-spectroscopy indicated that the crude product consisted of 99 P-% methanephosphonic acid dichloride and 1 P-% catalyst, at that moment.

EXAMPLE 7

(Comparative Example)

As described in Example 1, 297.5 g (2.5 mols) thionyl chloride heated to boiling was admixed within 2 hours with 124 g (1 mol) methanephosphonic acid dimethylester without catalyst addition. At the end of the dosing period, 31-P-NMR-spectroscopy indicated the existence of: methanephosphonic acid dichloride (4.4 P-%), methanephosphonic acid methylester chloride (46.2 P-%), polymethanephosphonic acid methylester and chlorides (49.4 P-%); for comparison see Example 1. After a 7 hour post reaction period of at boiling temperature, the reaction product was found to consist of methanephosphonic acid dichloride (13 P-%), methanephosphonic acid methylester chloride (0.3 P-%) and polymethanephosphonic acid chlorides (86.7 P-%).

EXAMPLE 8

(Comparative Example)

As described in the prior art and in Example 1, 124 g (1 mol) methanephosphonic acid dimethylester was added within 2 hours to a mixture of 297.5 g (2.5 mols) thionyl chloride and 0.8 g (0.01 mol) dimethylformamide heated to boiling. 31-P-NMR spectroscopy at the end of the dosing period indicated that the reaction product consisted of methanephosphonic acid dichloride (18.9 P-%), methanephosphonic acid methylester chloride (76.9 P-%), polymethanephosphonic acid methylester and chlorides (4.2 P-%); for comparison see Example 1. Whereas methanephosphonic acid dichloride was found to have formed quantitatively after a 2 hour post-reaction in Example 1, the following phosphonic acid derivatives were found to have formed at the same moment in the present Example (31-P-NMR-spectroscopy): methanephosphonic acid dichloride (51.5 P-%), methanephosphonic acid methylester chloride (30.9 P-%), polymethanephosphonic acid methylester and chlorides (17.6 P-%).

I claim:

1. Process for making phosphonic acid dichlorides of the formula I

in which R stands for straight or branched, optionally halogen-substituted alkyl group, alkenyl group, aralkyl group or aryl group having from 1 to 12 carbon atoms by reacting thionyl chloride with a phosphonic acid dialkylester of the formula II

in which R has the meaning given above and R' stands for a straight or branched, optionally halogen-substituted alkyl group having from 1 to 4 carbon atoms, in the presence of a catalyst, which comprises using, as the catalyst, a compound of the formulae III, IV or V

$$R^1R^2R^3 \qquad P \qquad (V)$$

in which $R^1$, $R^2$ and $R^3$ each stand for identical or different alkyl groups or aryl groups having from 1 to 8 carbon atoms, X stands for chloride or bromine, and $R^4$ has the same meaning as $R^1$ through $R^3$ or stands for chlorine or bromine wherein the phosphonic acid dialkylester, thionyl chloride and catalyst are used in a quantitative ratio of 1:2—3:0.001—0.1.

2. The process as claimed in claim 1, wherein the compound of formula III used as the catalyst is tetrabutyl phosphonium chloride or bromide.

3. The process as claimed in claim 1, wherein the compound of formula IV used as the catalyst is triphenyl phosphine.

4. The process as claimed in claim 1, wherein the compound of formula V used as the catalyst is trioctyl phosphine oxide.

5. The process as claimed in claim 1, wherein the phosphonic acid dialkylester, thionyl chloride and catalyst are used in a quantitative ratio of 1:2.5:0.01.

6. The process as claimed in claim 1, wherein the reaction is effected at a temperature of 70° to 150° C. at atmospheric pressure.

* * * * *